(12) United States Patent
Guan et al.

(10) Patent No.: US 10,807,967 B2
(45) Date of Patent: Oct. 20, 2020

(54) METHOD OF PREPARING N-ACYL ANTHRANILAMIDE

(71) Applicant: MAX (RUDONG) CHEMICALS CO., LTD., Nantong, Jiangsu (CN)

(72) Inventors: Baochuan Guan, Zhejiang (CN); Tianhao Zhang, Zhejiang (CN); Qiuju Sheng, Zhejiang (CN); Bangchi Chen, Zhejiang (CN)

(73) Assignee: MAX (RUDONG) CHEMICALS CO., LTD., Nantong (CN)

( * ) Notice: Subject to any disclaimer, the term of this patent is extended or adjusted under 35 U.S.C. 154(b) by 0 days.

(21) Appl. No.: 16/694,989

(22) Filed: Nov. 25, 2019

(65) Prior Publication Data

US 2020/0087278 A1    Mar. 19, 2020

Related U.S. Application Data

(63) Continuation of application No. PCT/CN2018/084008, filed on Apr. 23, 2018.

(30) Foreign Application Priority Data

May 26, 2017    (CN) .......................... 2017 1 0386998

(51) Int. Cl.
   *C07D 401/04*    (2006.01)
(52) U.S. Cl.
   CPC .................. *C07D 401/04* (2013.01)
(58) Field of Classification Search
   CPC .................................................... C07D 401/04
   USPC ....................................................... 546/275.4
   See application file for complete search history.

(56) References Cited

FOREIGN PATENT DOCUMENTS

| CN | 1541063 A | 10/2004 |
|----|-----------|---------|
| CN | 100425607 C | 10/2008 |
| CN | 103058993 A | 4/2013 |
| CN | 103304508 A | 9/2013 |
| CN | 103601718 A | 2/2014 |
| CN | 104003976 A | 8/2014 |
| CN | 107089970 A | 8/2017 |
| WO | 03015519 A1 | 2/2003 |
| WO | 03024222 A1 | 3/2003 |
| WO | 2008010897 A2 | 1/2008 |

*Primary Examiner* — Charanjit Aulakh
(74) *Attorney, Agent, or Firm* — Wayne & Ken, LLC; Tony Hom

(57) ABSTRACT

Disclosed herein is a method of preparing N-acyl anthranilamide (I), including: reacting a substituted anthranilic acid (II) with pyrazolecarboxylic acid (III) under the action of a phosphorus reagent and a base to obtain an intermediate benzoxazinone (IV); and subjecting the intermediate benzoxazinone (IV) and a protonic acid salt of methylamine to a ring-opening reaction to obtain N-acyl anthranilamide (I), as shown in the following reaction scheme:

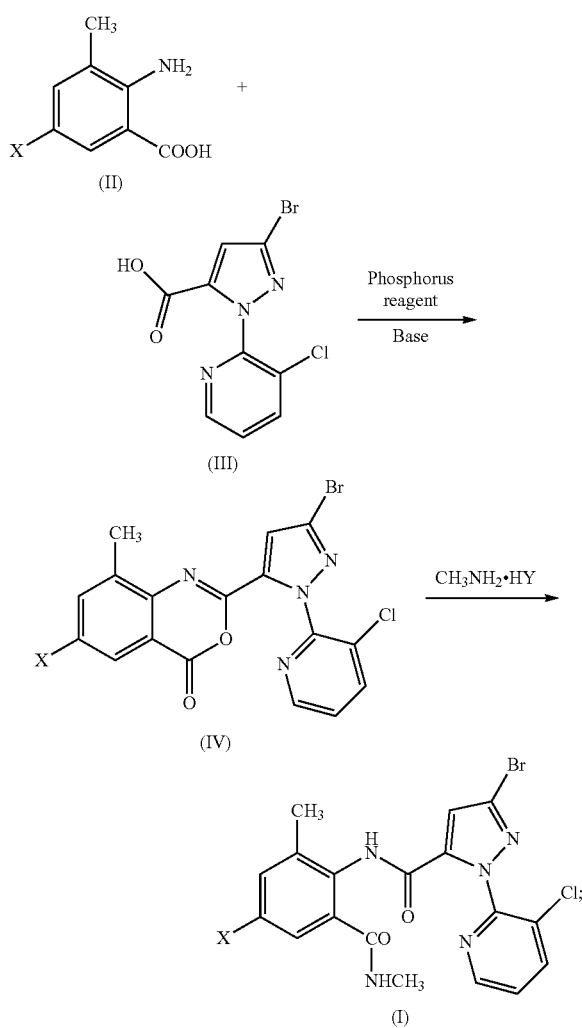

where X is hydrogen, chloro or cyano group; and HY is hydrohalic acid, sulfuric acid, phosphoric acid or a carboxylic acid. The method has the advantages of simple operation, mild reaction conditions, less waste and high overall yield, and thus is suitable for industrial production.

10 Claims, No Drawings

METHOD OF PREPARING N-ACYL ANTHRANILAMIDE

CROSS-REFERENCE TO RELATED APPLICATIONS

This application is a continuation of International Patent Application PCT/CN2018/084008, filed on Apr. 23, 2018, which claims the benefit of priority from Chinese Patent Application No. 201710386998.7, filed on May 26, 2017. The content of the aforementioned application, including any intervening amendments thereto, is incorporated herein by reference.

TECHNICAL FIELD

This application relates to organic synthesis, and more specifically to a method of preparing N-acyl anthranilamide.

BACKGROUND

N-Acyl anthranilamides (I) (as shown hereinafter) are an important class of organic compounds which are widely used in pesticides, medicines and other fields. For example, 3-bromo-N-(2-methyl-4-chloro-6-(carbamoyl)phenyl)-1-(3-chloro-2-pyridinyl)-1H-pyrazole-5-carboxamide (X is chloro, chlorantraniliprole) and 3-bromo-N-(2-methyl-4-cyano-6-(carbamoyl)phenyl)-1-(3-chloro-2-pyridinyl)-1H-pyrazole-5-carboxamide (X is cyano, cyantraniliprole) developed by DuPont Company are two important N-acyl anthranilamide insecticides, which mainly act on ryanodine receptors of insects and are used to control most chewing pests, especially Lepidoptera, Coleoptera and Diptera, and thus they are suitable for the pest control for fruit trees, vegetables, grape berries, cotton, sugar cane, rice, lawns and etc.

Currently, there are mainly three methods for synthesizing N-acyl anthranilamide (I) using a substituted anthranilic acid (II) and pyrazolecarboxylic acid (III) as raw materials.

In method 1, a substituted anthranilic acid (II) is dehydrated and cyclized under the action of a formyl chlorinating reagent (such as methyl chloroformate and phosgene) to obtain an intermediate isatoic anhydride (V), and pyrazolecarboxylic acid (III) is converted to pyrazolecarboxylic chloride (VI) under the action of thionyl chloride and DMF. Then, the isatoic anhydride (V) and pyrazolecarboxylic chloride (VI) are condensed under the action of an acid binding agent such as pyridine to give an intermediate benzoxazinone (IV). Then the latter undergoes further a ring-opening reaction with methylamine to produce N-acyl anthranilamide (I) (WO2003/015519). The reaction scheme is shown as follows:

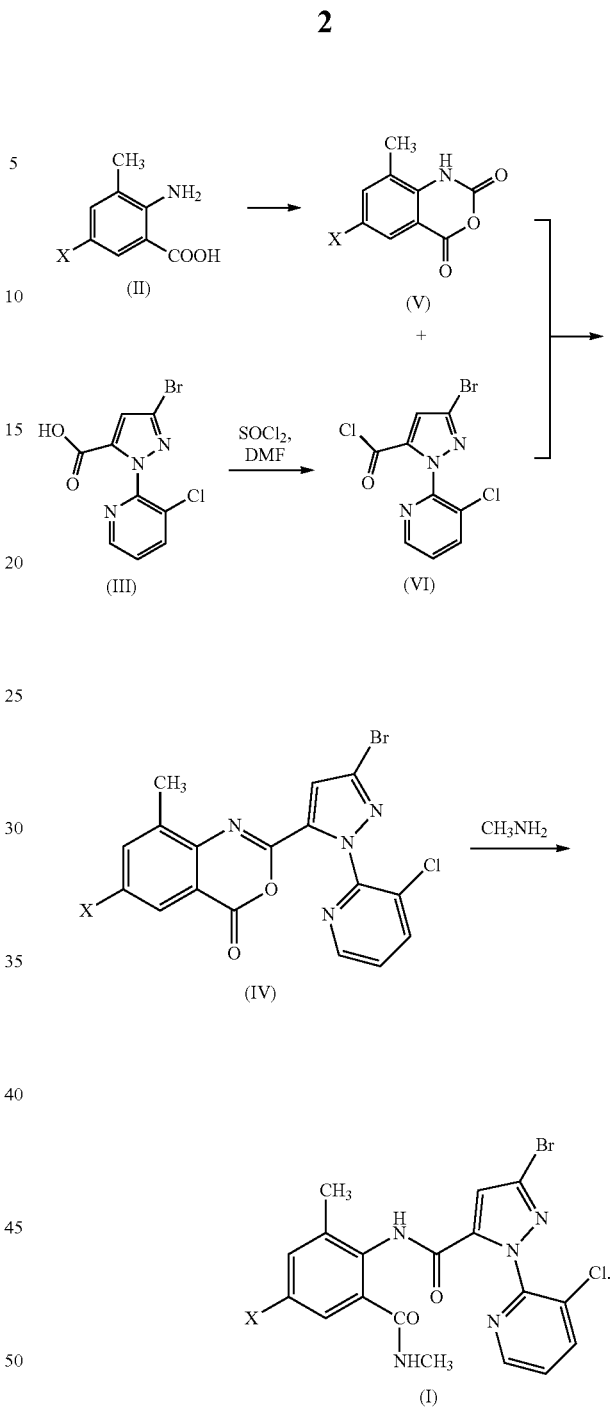

In method 2, a substituted anthranilic acid (II) is dehydrated and cyclized under the action of a formyl chlorinating reagent (such as methyl chloroformate and phosgene) to obtain an intermediate isatoic anhydride (V). The latter undergoes a ring-opening reaction with methylamine to give anthranilamide (VII). Pyrazolecarboxylic acid (III) is converted to pyrazolecarboxylic chloride (VI) under the action of thionyl chloride and DMF. Then the pyrazolecarboxylic chloride (VI) and the anthranilamide (VII) are condensed under an acid binding agent to produce N-acyl anthranilamide (I) (WO2008/010897). The reaction scheme is shown as follows:

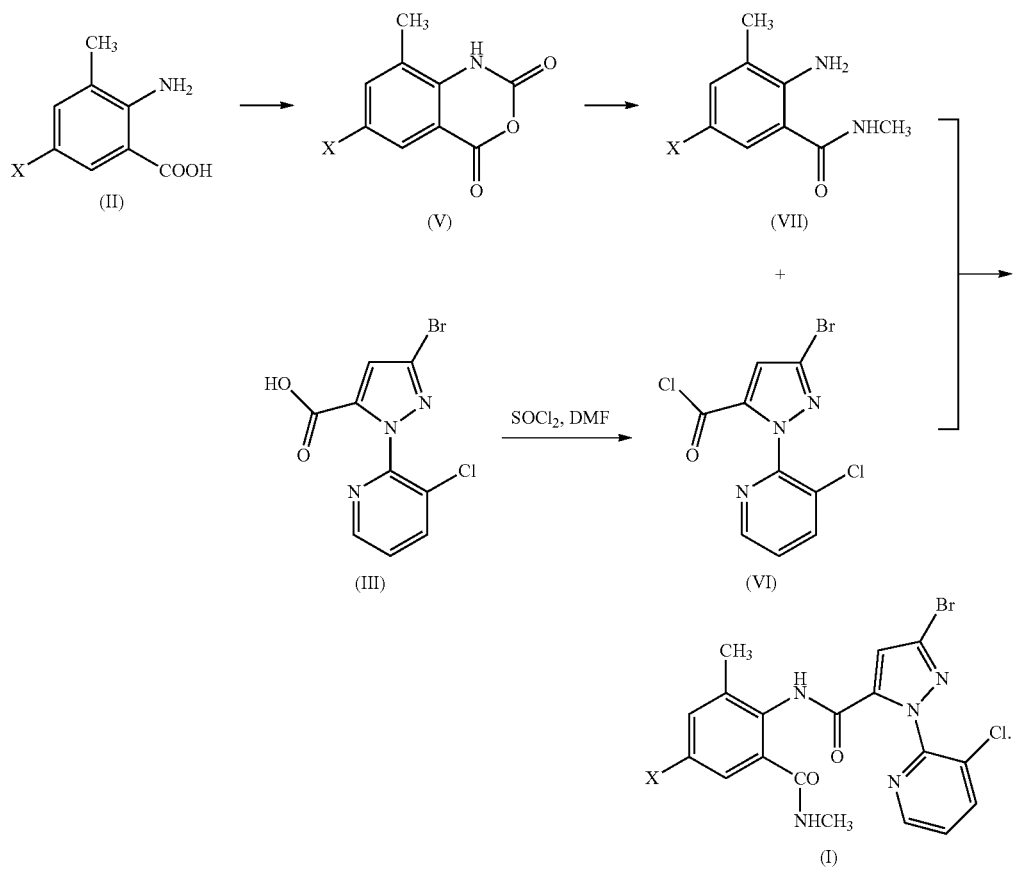

Methods 1 and 2 both have a relatively long reaction steps, and more over require highly-toxic reagents such as methyl chloroformate and phosgene, resulting in operational inconveniences and unsuitability for industrial production.

In method 3, a substituted anthranilic acid (II) is reacted with pyrazolecarboxylic acid (III) under the action of methanesulfonyl chloride and an acid binding agent to give an intermediate benzoxazinone (IV), which is then reacted with a solution of methylamine in tetrahydrofuran to obtain N-acyl anthranilamide (I) (WO2003/015519). The reaction scheme is specifically shown as follows:

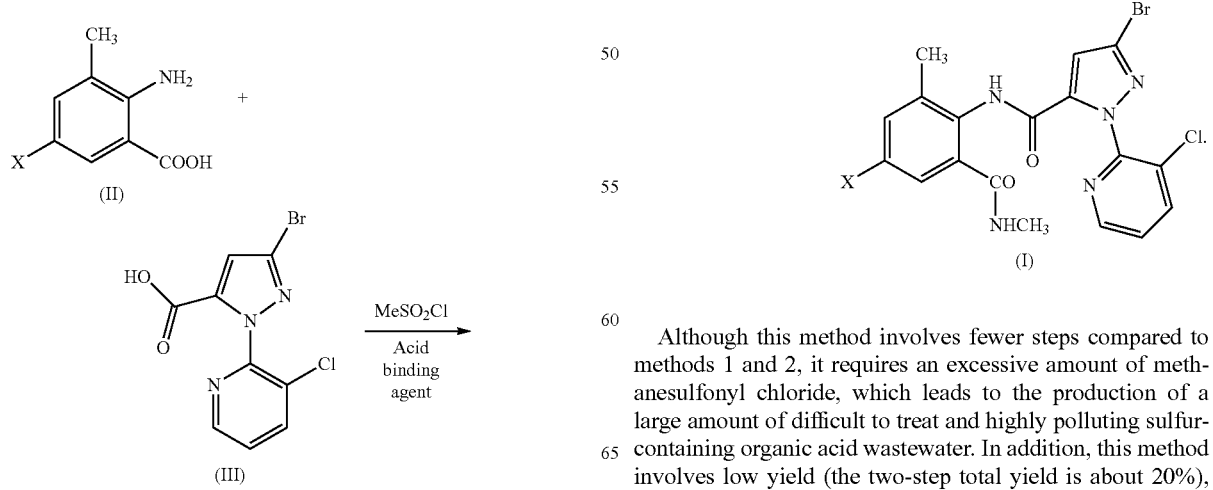

Although this method involves fewer steps compared to methods 1 and 2, it requires an excessive amount of methanesulfonyl chloride, which leads to the production of a large amount of difficult to treat and highly polluting sulfur-containing organic acid wastewater. In addition, this method involves low yield (the two-step total yield is about 20%), unsuitable for industrial production.

SUMMARY

This application provides a simpler, more environmentally-friendly and more efficient method of preparing N-acyl anthranilamide (I) to overcome the above drawbacks in the prior art.

This application provides a method of preparing N-acyl anthranilamide (I), comprising:

step (1) reacting a substituted anthranilic acid (II) with pyrazolecarboxylic acid (III) under the action of a phosphorus reagent and a base to obtain an intermediate benzoxazinone (IV); and step (2) subjecting the intermediate benzoxazinone (IV) and a protonic acid salt of methylamine to a ring-opening reaction to obtain N-acyl anthranilamide (I), as shown in the following reaction scheme:

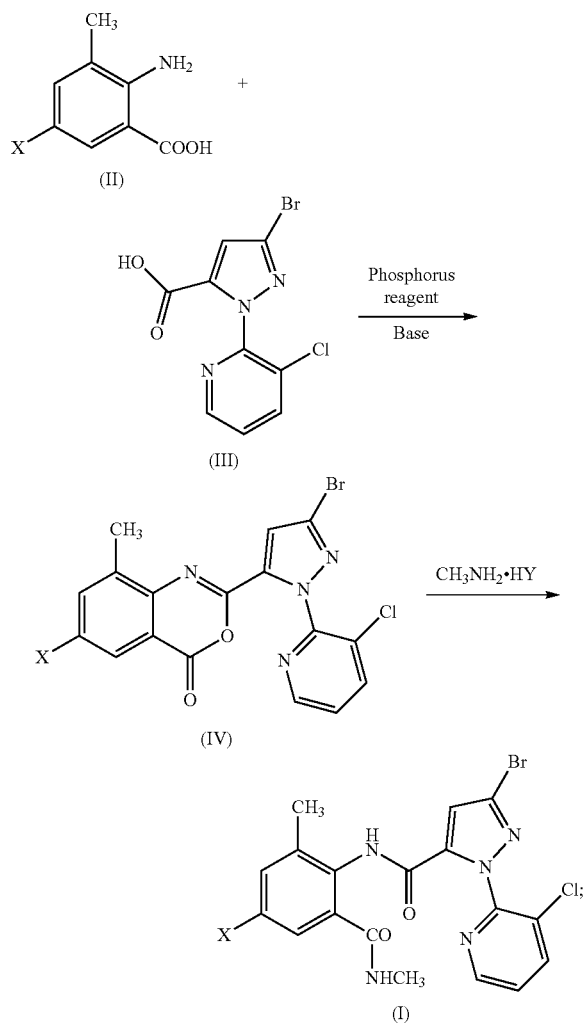

wherein:

X is hydrogen, chloro or cyano group; and

HY is hydrohalic acid, sulfuric acid, phosphoric acid or a carboxylic acid, preferably hydrochloric acid or sulfuric acid.

The phosphorus reagent is a phosphorus-containing compound, such as phosphorus oxychloride, phosphorus oxybromide, phosphorus trichloride, phosphorus tribromide, phosphorus pentachloride or phosphorus pentabromide, preferably phosphorus oxychloride or phosphorus oxybromide.

The base used in step (1) is an organic base or an inorganic base, preferably an organic base, and more preferably a tertiary amine base such as pyridine, 3-methylpyridine, N,N-dimethylaminopyridine and triethylamine.

In step (1), a molar ratio of the compound (II) to the compound (III) is 1:0.5-1.5; a molar ratio of the compound (II) to the phosphorus reagent is 1:1-2; and a molar ratio of the compound (II) to the base is 1:2-5.

In step (2), the ring opening reaction may be performed in the presence of an appropriate amount of a base, where the base is an organic base or an inorganic base, preferably an organic base such as triethylamine, pyridine and 3-methylpyridine, and a molar ratio of the compound (IV) to the base is 1:1-3.

A molar ratio of the compound (IV) to the protonic acid salt of methylamine is 1:1-3.

A solvent used herein is selected from N,N-dimethylformamide, acetone or acetonitrile, preferably acetonitrile.

Compared to the prior art, the method provided herein of preparing N-acyl anthranilamide has the following advantages.

(1) This method has simple process and mild reaction conditions.

(2) This method avoids the use of toxic substance such as methyl chloroformate or phosgene and is easy to operate.

(3) This method is free of production of sulfur-containing organic acid wastewater caused by organic reagent, such as methanesulfonyl chloride, and has less pollution.

(4) This method is high yielding, suitable for industrial production.

DETAILED DESCRIPTION OF EMBODIMENTS

Features of this application will be further illustrated below with reference to the embodiments, but these embodiments are not intended to limit this application.

Example 1 Preparation of 3-bromo-N-(2-methyl-4-chloro-6-(carbamoyl) phenyl)-1-(3-chloro-2-pyridinyl)-1H-pyrazole-5-carboxamide (chlorantraniliprole)

Step (1)

3.02 g of 3-bromo-1-(3-chloro-2-pyridinyl)-1H-pyrazole-5-carboxylic acid, 1.95 g of 3-methylpyridine and 15 mL of acetonitrile were added to a 100 mL three-necked flask, to which 5.73 g of POBr₃ was dropwise added at −5° C. The reaction mixture was stirred for 0.5 h with the temperature kept, and then 1.86 g of 2-amino-3-methyl-5-chlorobenzoic acid was added. The reaction mixture was reacted at room temperature for 1 h. After the reaction was complete, the reaction mixture was added with 20 mL of water, stirred for 0.5 h and filtered. The filter cake was washed with a mixture of acetonitrile and water in a ratio of 3:2 and dried to give 4.16 g of 2-[3-bromo-1-(3-chloro-2-pyridinyl)-1H-pyrazol-5-yl]-6-chloro-8-methyl-4H-3,1-benzoxazine-4-one, and the yield was 92%.

Step (2)

4.16 g of 2-[3-bromo-1-(3-chloro-2-pyridinyl)-1H-pyrazol-5-yl]-6-chloro-8-methyl-4H-3,1-benzoxazine-4-one obtained in step (1) was dissolved in 20 mL of acetonitrile, to which 0.92 g of methylamine hydrochloride was added. The reaction mixture was stirred at room temperature for 4 h, desolventized under vacuum, washed with water and dried to give 3.56 g of chlorantraniliprole, and the yield was 80%.

Example 2 Preparation of 3-bromo-N-(2-methyl-4-chloro-6-(carbamoyl) phenyl)-1-(3-chloro-2-pyridinyl)-1H-pyrazole-5-carboxamide (chlorantraniliprole)

Step (1)

3.02 g of 3-bromo-1-(3-chloro-2-pyridinyl)-1H-pyrazole-5-carboxylic acid, 1.95 g of 3-methylpyridine and 15 mL of acetonitrile were added to a 100 mL three-necked flask, to which 5.73 g of POBr$_3$ was dropwise added at −5° C. The reaction mixture was stirred for 0.5 h with the temperature kept, and then 1.86 g of 2-amino-3-methyl-5-chlorobenzoic acid was added. The reaction mixture was reacted at room temperature for 1 h. After the reaction was complete, the reaction mixture was added with 20 mL of water, stirred for 0.5 h and filtered. The filter cake was washed with a mixture of acetonitrile and water in a ratio of 3:2 and dried to give 4.16 g of 2-[3-bromo-1-(3-chloro-2-pyridinyl)-1H-pyrazol-5-yl]-6-chloro-8-methyl-4H-3,1-benzoxazine-4-one, and the yield was 92%.

Step (2)

4.16 g of 2-[3-bromo-1-(3-chloro-2-pyridinyl)-1H-pyrazol-5-yl]-6-chloro-8-methyl-4H-3,1-benzoxazine-4-one obtained in step (1) was dissolved in 20 mL of acetonitrile, to which 1.11 g of triethylamine and 0.92 g of methylamine hydrochloride were added. The reaction mixture was stirred at room temperature for 2 h, desolventized under vacuum, washed with water and dried to give 4.18 g of chlorantraniliprole, and the yield was 94%.

Example 3 Preparation of 3-bromo-N-(2-methyl-4-chloro-6-(carbamoyl) phenyl)-1-(3-chloro-2-pyridinyl)-1H-pyrazole-5-carboxamide (chlorantraniliprole)

Step (1)

4.53 g of 3-bromo-1-(3-chloro-2-pyridinyl)-1H-pyrazole-5-carboxylic acid, 1.58 g of pyridine and 15 mL of acetonitrile were added to a 100 mL three-necked flask, to which 3.07 g of POCl$_3$ was dropwise added at −5° C. The reaction mixture was stirred for 0.5 h with the temperature kept, and then 1.86 g of 2-amino-3-methyl-5-chlorobenzoic acid was added. The reaction mixture was reacted at room temperature for 0.5 h. After the reaction was complete, the reaction mixture was added with 20 mL of water, stirred for 0.5 h and filtered. The filter cake was washed with a mixture of acetonitrile and water in a ratio of 3:2, and dried to give 4.07 g of 2-[3-bromo-1-(3-chloro-2-pyridinyl)-1H-pyrazol-5-yl]-6-chloro-8-methyl-4H-3,1-benzoxazine-4-one, and the yield was 90%.

Step (2)

4.07 g of 2-[3-bromo-1-(3-chloro-2-pyridinyl)-1H-pyrazol-5-yl]-6-chloro-8-methyl-4H-3,1-benzoxazine-4-one obtained in step (1) was dissolved in 20 mL of acetonitrile, to which 2.73 g of triethylamine, pyridine and 1.82 g of methylamine hydrochloride were added. The reaction mixture was stirred at room temperature for 2 h, desolventized under vacuum, washed with water and dried to give 4.17 g of chlorantraniliprole, and the yield was 96%.

Example 4 Preparation of 3-bromo-N-(2-methyl-4-chloro-6-(carbamoyl) phenyl)-1-(3-chloro-2-pyridinyl)-1H-pyrazole-5-carboxamide (chlorantraniliprole)

Step (1)

3.02 g of 3-bromo-1-(3-chloro-2-pyridinyl)-1H-pyrazole-5-carboxylic acid, 4.87 g of 3-methylpyridine and 30 mL of acetonitrile were added to a 100 mL three-necked flask, to which 5.73 g of POBr$_3$ was dropwise added at −5° C. The reaction mixture was stirred for 0.5 h with the temperature kept, and then 1.86 g of 2-amino-3-methyl-5-chlorobenzoic acid was added. The reaction mixture was reacted at room temperature for 1.5 h. After the reaction was complete, the reaction mixture was added with 20 mL of water, stirred for 0.5 h and filtered. The filter cake was washed with a mixture of acetonitrile and water in a ratio of 3:2, and dried to give 4.2 g of 2-[3-bromo-1-(3-chloro-2-pyridinyl)-1H-pyrazol-5-yl]-6-chloro-8-methyl-4H-3,1-benzoxazine-4-one, and the yield was 93%.

Step (2)

4.2 g of 2-[3-bromo-1-(3-chloro-2-pyridinyl)-1H-pyrazol-5-yl]-6-chloro-8-methyl-4H-3,1-benzoxazine-4-one obtained in step (1) was dissolved in 20 mL of acetonitrile, to which 1.23 g of 4-dimethylaminopyridine and 2.18 g of methylamine sulfate were added. The reaction mixture was stirred at room temperature for 2.5 h, desolventized under vacuum, washed with water and dried to give 4.27 g of chlorantraniliprole, and the yield was 95%.

Example 5 Preparation of 3-bromo-N-(2-methyl-4-chloro-6-(carbamoyl) phenyl)-1-(3-chloro-2-pyridinyl)-1H-pyrazole-5-carboxamide (chlorantraniliprole)

Step (1)

3.02 g of 3-bromo-1-(3-chloro-2-pyridinyl)-1H-pyrazole-5-carboxylic acid, 1.95 g of 3-methylpyridine and 15 mL of acetonitrile were added to a 100 mL three-necked flask, to which 5.73 g of POBr$_3$ was dropwise added at −5° C. The reaction mixture was stirred for 0.5 h with the temperature kept, and then 1.86 g of 2-amino-3-methyl-5-chlorobenzoic acid was added. The reaction mixture was reacted at room temperature for 1 h. After the reaction was complete, the reaction mixture was added with 20 mL of water, stirred for 0.5 h and filtered. The filter cake was washed with a mixture of acetonitrile and water in a ratio of 3:2 and dried to give 4.16 g of 2-[3-bromo-1-(3-chloro-2-pyridinyl)-1H-pyrazol-5-yl]-6-chloro-8-methyl-4H-3,1-benzoxazine-4-one, and the yield was 92%.

Step (2)

4.16 g of 2-[3-bromo-1-(3-chloro-2-pyridinyl)-1H-pyrazol-5-yl]-6-chloro-8-methyl-4H-3,1-benzoxazine-4-one obtained in step (1) was dissolved in 20 mL of acetonitrile, to which 0.79 g of pyridine and 0.92 g of methylamine hydrochloride were added. The reaction mixture was stirred at room temperature for 1.5 h, desolventized under vacuum, washed with water and dried to give 4 g of chlorantraniliprole, and the yield was 90%.

Example 6 Preparation of 3-bromo-N-(2-methyl-4-cyano-6-(carbamoyl) phenyl)-1-(3-chloro-2-pyridinyl)-1H-pyrazole-5-carboxamide (cyantraniliprole)

Step (1)

3.02 g of 3-bromo-1-(3-chloro-2-pyridinyl)-1H-pyrazole-5-carboxylic acid, 1.95 g of 3-methylpyridine and 15 mL of acetonitrile were added to a 100 mL three-necked flask, to which 3.23 g of POCl$_3$ was dropwise added at −5° C. The reaction mixture was stirred for 0.5 h with the temperature kept, and 1.94 g of 2-amino-3-methyl-5-cyanobenzoic acid was added. The reaction mixture was reacted at room temperature for 2 h. After the reaction was complete, the reaction mixture was added with 20 mL of water, stirred for 0.5 h and filtered. The filter cake was washed with a mixture of acetonitrile and water in a ratio of 3:2 and dried to give 3.81 g of 2-[3-bromo-1-(3-chloro-2-pyridinyl)-1H-pyrazol-5-yl]-6-cyano-8-methyl-4H-3,1-benzoxazine-4-one, and the yield was 86%.

$^1$H NMR (500 MHz, DMSO): δ8.63 (dd, 1H), 8.40-8.33 (m, 2H), 8.10 (s, 1H), 7.77 (dd, 1H), 7.60 (s, 1H), 1.73 (s, 3H).

Step (2)

3.81 g of 2-[3-bromo-1-(3-chloro-2-pyridinyl)-1H-pyrazol-5-yl]-6-cyano-8-methyl-4H-3,1-benzoxazine-4-one obtained in step (1) was dissolved in 20 mL of acetonitrile, to which 1.11 g of triethylamine and 2.18 g of methylamine sulfate were added. The reaction mixture was stirred at room temperature for 2.5 h, desolventized under vacuum, washed with water and dried to give 3.87 g of cyantraniliprole, and the yield was 95%.

Example 7 Preparation of 3-bromo-N-(2-methyl-4-cyano-6-(carbamoyl) phenyl)-1-(3-chloro-2-pyridinyl)-1H-pyrazole-5-carboxamide (cyantraniliprole)

Step (1)

3.02 g of 3-bromo-1-(3-chloro-2-pyridinyl)-1H-pyrazole-5-carboxylic acid, 1.95 g of 3-methylpyridine and 15 mL of acetonitrile were added to a 100 mL three-necked flask to which 1.62 g of POCl$_3$ was dropwise added at −5° C. The reaction mixture was stirred for 0.5 h with the temperature kept, and 3.88 g of 2-amino-3-methyl-5-cyanobenzoic acid was added. The reaction mixture was reacted at room temperature for 1.5 h. After the reaction was complete, the reaction mixture was added with 20 mL of water, stirred for 0.5 h and filtered. The filter cake was washed with a mixture of acetonitrile and water in a ratio of 3:2 and dried to give 4.17 g of 2-[3-bromo-1-(3-chloro-2-pyridinyl)-1H-pyrazol-5-yl]-6-cyano-8-methyl-4H-3,1-benzoxazine-4-one, and the yield was 88%.

Step (2)

4.17 g of 2-[3-bromo-1-(3-chloro-2-pyridinyl)-1H-pyrazol-5-yl]-6-cyano-8-methyl-4H-3,1-benzoxazine-4-one obtained in step (1) was dissolved in 20 mL of acetonitrile, to which 1.78 g of triethylamine pyridine and 2.82 g of methylamine sulfate were added. The reaction mixture was stirred at room temperature for 2.5 h, desolventized under vacuum, washed with water and dried to give 4.08 g of cyantraniliprole, and the yield was 98%.

What is claimed is:

1. A method of preparing N-acyl anthranilamide (I), comprising:
   step (1) reacting a substituted anthranilic acid (II) with pyrazolecarboxylic acid (III) under the action of a phosphorus reagent and a base to obtain an intermediate benzoxazinone (IV); and
   step (2) subjecting the intermediate benzoxazinone (IV) and a protonic acid salt of methylamine to a ring-opening reaction to obtain N-acyl anthranilamide (I), as shown in the following reaction scheme:

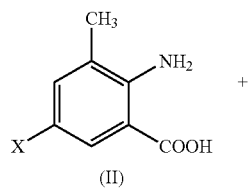

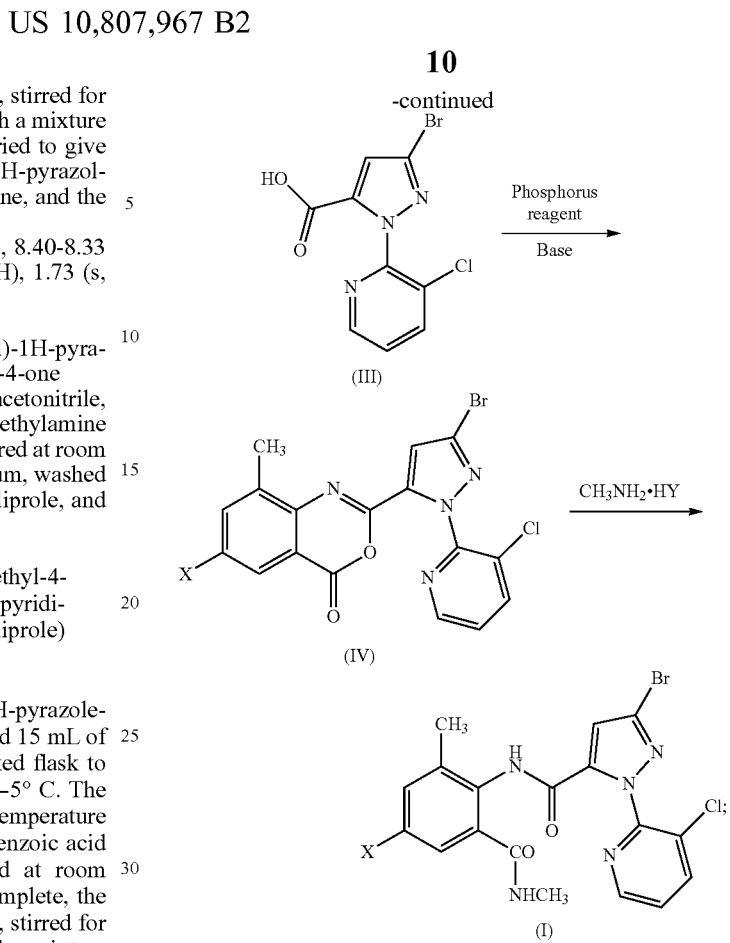

wherein:
X is hydrogen, chloro or cyano group; and
HY is hydrohalic acid, sulfuric acid, phosphoric acid or a carboxylic acid.

2. The method according to claim 1, characterized in that the phosphorus reagent is phosphorus oxychloride, phosphorus oxybromide, phosphorus trichloride, phosphorus tribromide, phosphorus pentachloride or phosphorus pentabromide.

3. The method according to claim 2, characterized in that the phosphorus reagent is phosphorus oxychloride or phosphorus oxybromide.

4. The method according to claim 1, characterized in that in step (1), the base is an organic base.

5. The method according to claim 4, characterized in that the organic base is pyridine, 3-methylpyridine, N,N-dimethylaminopyridine or triethylamine.

6. The method according to claim 1, characterized in that HY is hydrochloric acid or sulfuric acid.

7. The method according to claim 1, characterized in that in step (1), a molar ratio of the compound (II) to the compound (III) is 1:0.5-1.5; a molar ratio of the compound (II) to the phosphorus reagent is 1:1-2; and a molar ratio of the compound (II) to the base is 1:2-5.

8. The method according to claim 1, characterized in that the step (2) is carried out in the presence of a base.

9. The method according to claim 8, characterized in that the base is triethylamine, pyridine or 3-methylpyridine.

10. The method according to claim 1, characterized in that in step (2), a molar ratio of the compound (IV) to the protonic acid salt of methylamine is 1:1-3; and a molar ratio of the compound (IV) to the base is 1:1-3.

* * * * *